United States Patent [19]

Hasson

[11] Patent Number: 4,724,838

[45] Date of Patent: Feb. 16, 1988

[54] FOOTED FORCEPS-TYPE SURGICAL INSTRUMENT

[76] Inventor: Harrith M. Hasson, P.O. Box 14898, Chicago, Ill. 60614

[21] Appl. No.: 914,194

[22] Filed: Oct. 1, 1986

[51] Int. Cl.[4] ............................................. A61B 17/28
[52] U.S. Cl. .................................... 128/321; 128/325; 128/354
[58] Field of Search ............................... 128/321–322, 128/334 R, 340, 325, 354

[56] References Cited

U.S. PATENT DOCUMENTS

| | | | |
|---|---|---|---|
| 1,615,125 | 1/1927 | Lespinasse | 128/354 X |
| 2,109,147 | 2/1938 | Grosso | 128/321 |
| 2,665,692 | 1/1954 | L'esperance | 128/334 R |

FOREIGN PATENT DOCUMENTS 2073083 10/1981 United Kingdom ................ 128/321

Primary Examiner—Dalton L. Truluck
Attorney, Agent, or Firm—Wood, Dalton, Phillips, Mason & Rowe

[57] ABSTRACT

A forceps-type surgical instrument which includes a pair of forceps blades coupled together at their proximal ends and spreadable and closable at their distal ends. A pair of feet are respectively mounted on the distal ends of the blades and extend transversely outwardly of the blades to enlarge the working area of the blades and to facilitate the application of counter-pressures during surgical operations. At least one aperture is formed through at least one of the feet for receiving and guiding a needle, suture or the like therethrough at a point offset from the plane of the forceps blades.

37 Claims, 14 Drawing Figures

U.S. Patent    Feb. 16, 1988    Sheet 1 of 2    4,724,838
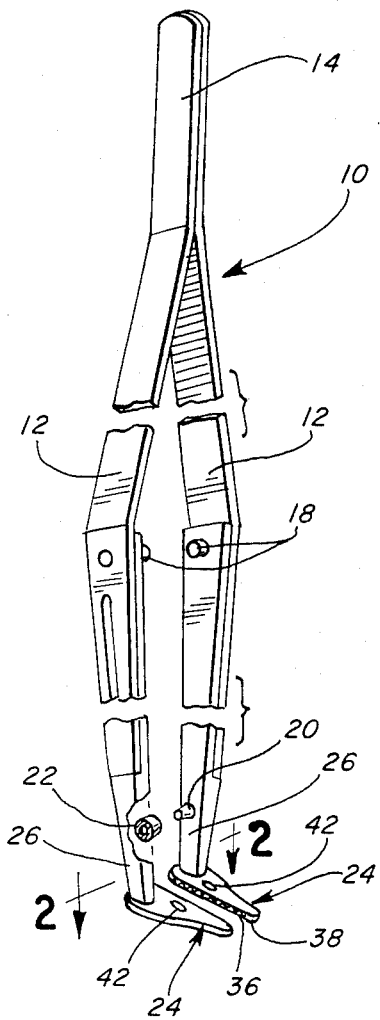
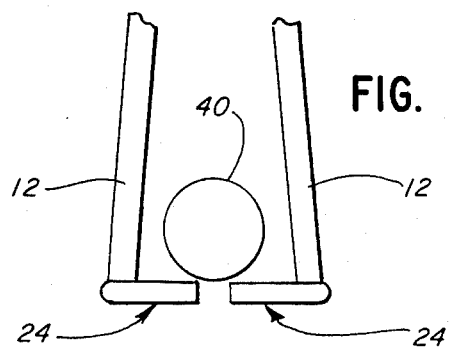
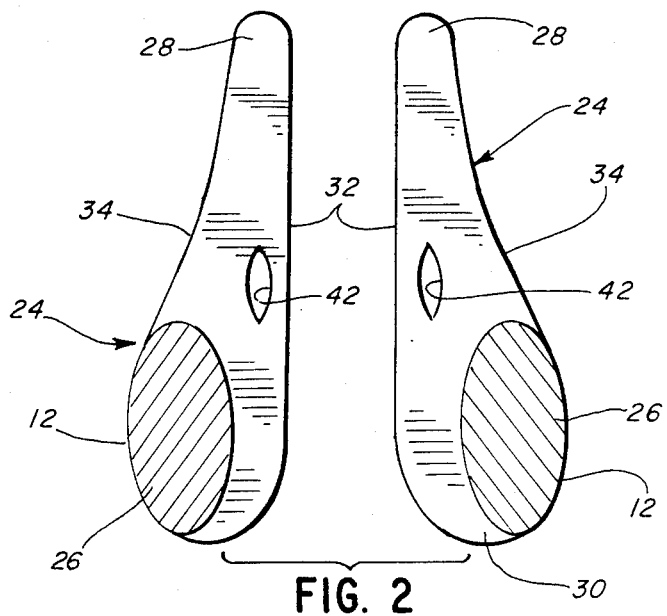
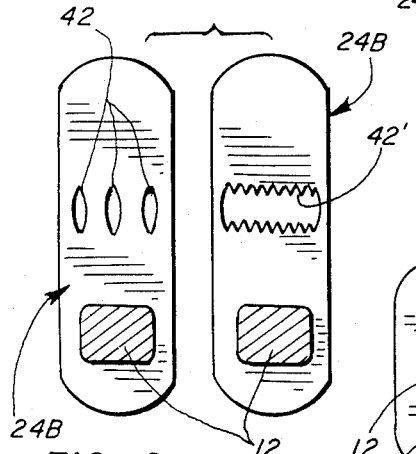
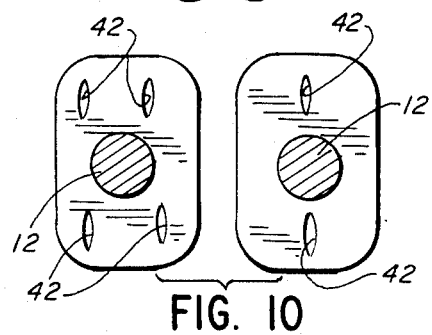
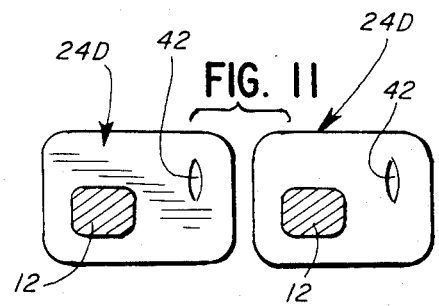
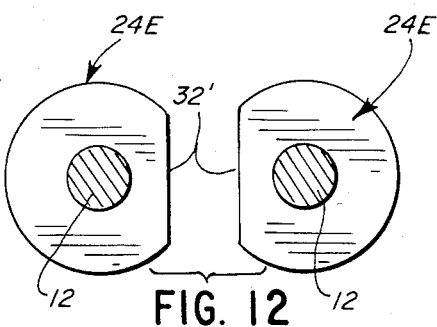

FOOTED FORCEPS-TYPE SURGICAL INSTRUMENT

FIELD OF THE INVENTION

This invention generally relates to surgical or medical instruments of the forceps-type conventionally used for grasping and manipulating body tissues or organs.

BACKGROUND OF THE INVENTION

Conventional forceps-type instruments of the character described normally include a pair of forceps blades which function in a tweezer-like action and are used in medical operations or surgery to hold, expose and manipulate tissues. Such instruments normally include two blades joined or jointed at proximal ends for moving their distal ends toward and away from each other in a closing and opening action. The distal ends of the blades comprise functional jaws which either are formed integral with the blades or built and mounted as inlays on the distal ends of the blades. The handle portions of the blades may be straight, angular or offset, take the shape of a bayonet or comprise the handles of a scissor-type instrument.

The success of microsurgery depends on gentle tissue handling, avoidance of trauma and meticulous and accurate approximation and apposition of tissues. It is known that exposing and handling tissue through application of counter-pressure is much more desirable than grasping the tissue between the jaws of a forceps, a tissue forceps or a tweezer-type platform. Such grasping or direct pressure application, regardless of how gentle, more often than not results in microscopic hemorrhages and tissue abrasion and trauma.

This invention is directed to providing a new and improved forceps-type surgical instrument capable of applying smooth atraumatic external or internal counter-pressure with an extended surface on tissues especially those handled in microsurgery, to facilitate manipulation of the tissues, and exposure and passage of needles through the tissues while maintaining proper orientation of the needle for subsequent suturing.

SUMMARY OF THE INVENTION

An object, therefore, of the invention is to provide a new and improved forceps-type surgical instrument which can be used for various tissue manipulations, the instrument being capable of delicately holding, restraining and stabilizing tissues by external or internal counter-pressure without requiring tissue grasping.

In the exemplary embodiment of the invention, the forceps-type surgical instrument includes a pair of forceps blades coupled together at their proximal ends and spreadable and closable at their distal ends. The forceps blades may be incorporated in simple spring-loaded V-shaped configurations of different designs, such as straight, angular or offset, or take the shape of a bayonet. The blades also may be incorporated in a hinged or pivoted scissors-like instrument.

Generally, a pair of feet are respectively mounted on the distal ends of the forceps blades, with the feet extending transversely outwardly of the blades to enlarge the working area thereof and to facilitate the application of counter-pressures during surgical operations.

Preferably, the feet are generally flat in a plane generally perpendicular to the forceps blades. The feet have forward or anterior ends or tips, rearward or posterior ends, inwardly facing medial edges and outwardly facing lateral edges. Preferably, the medial edges are generally parallel to each other and may be serrated to enhance the grasping of needles or sutures. The lateral edges are smooth and polished to glide smoothly over tissues, particularly when the forceps is in use in stretching or spreading tissues.

A feature of the invention comprises at least one aperture in at least one of the feet of the forceps blades for receiving and guiding a needle, suture or the like during operations therewith. There are a variety of locations and configurations of apertures disclosed herein for various intended functions.

A further feature of the invention comprises an optional flexible or articulated junction between the blades of the forceps and the feet to permit relative movement in infinite directions or in a plate so as to accommodate the plane of each foot to the surface being sutured.

Other objects, features and advantages of the invention will be apparent from the following detailed description taken in connection with the accompanying drawings.

DESCRIPTION OF THE DRAWINGS

The features of this invention which are believed to be novel are set forth with particularity in the appended claims. The invention, together with its objects and the advantages thereof, may be best understood by reference to the following description taken in conjunction with the accompanying drawings, in which like reference numerals identify like elements in the figures and in which:

FIG. 1 is a perspective view, partially broken away, illustrating a forceps-type surgical instrument incorporating the concepts of the invention;

FIG. 2 is a horizontal section, on an enlarged scale, taken generally along line 2—2 of FIG. 1, through the distal ends of the forceps blades, illustrating a top plan view of the forceps feet;

FIG. 3 is a fragmented rear elevational view of the distal end of the instrument;

FIGS. 8–12 are horizontal sectional views similar to that of FIG. 2, through the distal ends of the forceps blades, and illustrating various configurations of feet and various locations for the guiding apertures through the feet;

DETAILED DESCRIPTION OF THE PREFERRED EMBODIMENT

Figure 4:
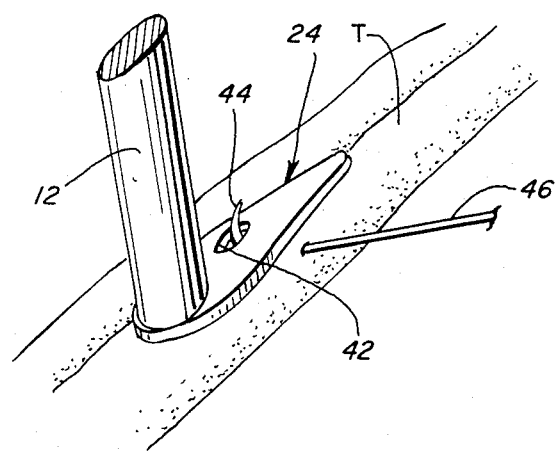
FIG. 4 is a perspective view illustrating one of the feet at the distal end of one of the forceps blades being used to apply counter-pressure to tissue and guiding a needle during a suturing operation.

Referring to the drawings in greater detail, and first to FIG. 1, a forceps-type surgical instrument is illustrated and generally designated 10. The instrument includes a pair of forceps blades 12 fixed together at their proximal ends 14. The blades are fabricated of metal or like material so as to be self-spring-biased toward a spread or open condition as illustrated. Restraining bosses 18 may be provided on the inside faces of the forceps blades to control closing pressure. A pin 20 and aperture 22 restraining device also may be provided on the inside faces of the forceps blades to prevent lateral shifting of the blades when in closed condition.

Generally, the invention contemplates the incorporation of a pair of feet, generally designated 24, mounted on the distal ends 26 of forceps blades 12, the feet extending transversely outwardly of the blades to enlarge the working area thereof and to facilitate the application of counter-pressures during surgical operations, as described hereinafter.

More particularly, referring to FIG. 2, one configuration of feet 24 is shown in greater detail. In this embodiment, the feet are generally flat in a plane generally perpendicular to the distal ends 26 of forceps blades 12. For better reference purposes hereinafter, each foot 24 includes a forward or anterior end or tip 28, a rearward or posterior end or tip 30, an inwardly facing or medial edge 32 and an outwardly facing or lateral edge 34. Preferably, the inwardly facing medial edges of the pair of feet 24 extend generally parallel to each other.

In the embodiment illustrated in FIGS. 1 and 2, feet 24 are mounted to the distal ends 26 of forceps blades 12 close to or at the lateral edges and posterior tip of the feet to allow the instrument to function as a tubal forceps, as described hereinafter, by restraining and stabilizing a tube-like structure or organ between the medial edges 32. Medial edges 32 are serrated, as at 36 (FIG. 1) to facilitate the holding of sutures or less delicate tissues and to make the holding or grasping more secure and less tenuous. The serrations do not extend all the way to the anterior tips of the feet to provide smooth medial edge portions 38 (FIG. 1) for holding more delicate structures with a smooth surface. Lateral edges 34 are smooth and polished to glide smoothly over tissue when the forceps is in use for stretching or spreading tissues, such as in the application of internal counter-pressure. The rounded edges about anterior tips 28 also are smooth and narrow, as shown, to allow access into very small tubes for the purpose of spreading the tubes in a counter-pressure action. Such spreading action also is enhanced by the rearwardly diverging configuration of lateral edges 34.

FIG. 3 shows, somewhat schematically, the inward projection of feet 24 relative to forceps blades 12 for closing beneath a tubular structure 40 for purposes of gently lifting or stabilizing the structure.

Figure 5:
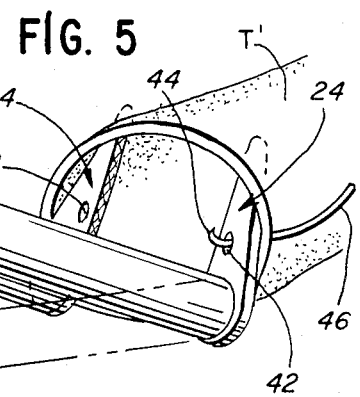
FIG. 5 is a view of both feet at the distal ends of the forceps blades applying internal counter-pressure to a tubular organ, again guiding the needle during a suturing operation.

Referring to FIGS. 4 and 5 in conjunction with FIG. 2, a feature of the invention is the provision of at least one aperture 42 formed through one or both feet 24. The apertures are provided for guiding needles, sutures and the like during operations therewith. As seen in FIG. 2, the apertures are generally "eye-shaped" and set along th longitudinal axis of the feet 12 so that the central portion of the apertures are wider than either end. The centers of the apertures are wide enough to easily receive needles such as microsurgical needles fitted to sutures from 5-0 to 10-0 size. The pointed or narrowed ends of the apertures are provided for exerting frictional gripping forces on the needles or sutures. In addition, the V-shapes of the aperture ends thereby can accommodate different sizes of needles.

FIG. 4 illustrates the use of the invention as stabilizing and applying counter-pressure to tissue "T" which is being sutured by a needle 44 and suture thread 46. After the needle is passed through the tissue, the needle is directed through aperture 42 and constrained or gripped by the V-shaped end of the aperture. Once secure, the needle is pulled out of tissue "T" and prepared for the following suture. This results in uninterrupted coordination between the two hands of a surgeon. One hand places the needle and suture through the tissue wall or surface which is stabilized by the external counter-pressure function of one or both of feet 24 of the forceps held by the surgeon's second hand. This hand holding the forceps, pulls the needle and suture out of the operative field, maintaining proper orientation of the needle and delivers the needle into the vicinity of a needle holder held by the first hand. The open needle holder then receives the needle positioned in proper orientation and the process is continued and repeated, as is appropriate. This coordination between the two hands keeps unnecessary awkward motions to a minimum and speeds up the operation. This also prevents loss, misplacement or lack of exposure of the needle, maintains proper orientation of the needle, expedites removal of the needle from the operative field and prepares the needle for recapture by the needle holder in one continuous simple motion. These unique features are made possible by the fact that the eye of the forceps designed to capture a microneedle is set in a plane opposite of that of the forceps blades themselves.

FIG. 5 shows both feet 24 at the distal ends of forceps blades 12 being used for spreading a tube-like structure "T'", again by applying counter-pressure using the outer, lateral edges of the feet. The operation of the forceps, the guiding and capturing of the needle, and the coordination between the surgeon's hands and the various instruments are substantially the same as described in relation to FIG. 4.

Figure 6:
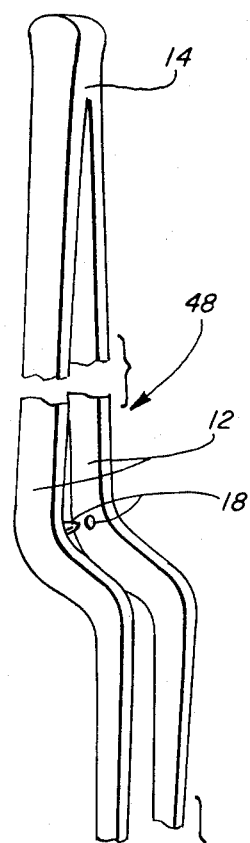
FIG. 6 is a perspective view, similar to that of FIG. 1, of the invention incorporated in a different type of forceps instrument.

FIG. 6 illustrates the invention incorporated in another form of forceps-type instrument, generally designated 48. This instrument includes an angular or offset portion 50 in forceps blades 12. Otherwise, the function and operation of feet 24 for use with the instrument is substantially the same as described in relation to FIGS. 1-5, and like numerals have been applied to like components where applicable.

Figure 7:
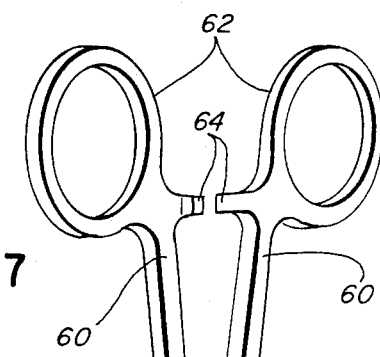
FIG. 7 is a perspective view illustrating the invention incorporated in a scissors-type forceps instrument.

FIG. 7 illustrates the invention incorporated in a further type of instrument, generally designated 52, which is a scissors-type forceps. This instrument includes blades 54 hinged or pivoted, as at 56, intermediate the distal ends 58 and proximal ends 60 thereof. As is conventional, rings 62 are formed on the proximal ends of the blades for receiving a surgeon's thumb and, another finger. Conventional lock means 64 are provided between rings 62. Again, feet 24 are provided on the tips of distal ends 58 and are used for applying counter-pressures and other operations described above.

The illustration of FIG. 7 is shown to emphasize the fact that the use of the term "forceps" in describing a surgical instrument herein is intended to encompass a wide variety of surgical instruments wherein the use of feet 24 is applicable, and it is not intended herein to limit the invention to any particular type of instrument, such as the spring-type forceps instruments shown in FIGS. 1 and 6. For instance, distal ends 58 of the scissors-type instrument in FIG. 7 are effectively the "forceps blades". Furthermore, it is contemplated that feet 24 may be mounted to the distal ends 26 of forceps blades 12 (FIGS. 1 and 6) or distal ends 58 of blades 54 (FIG. 7) by means of jointed constructions, such as ball-and-socket constructions as shown in FIG. 14 or resilient constructions such as shown in FIG. 13.

Figure 14:
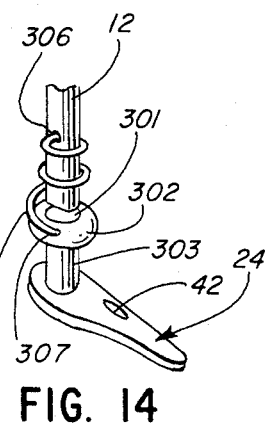
FIG. 14 is a perspective view illustrating the foot at the distal end of one of the forceps blades being connected together by a ball and socket connection with a resilient means for returning the foot to a predetermined orientation.

In FIG. 14 a ball 301 is mounted on the end of blade 12 with a socket 302 mounted on the stub 303 of a blade fixed to the foot 34. Optionally a coil spring 305 could be anchored at one end 306 to the blade 12 and at the other end 307 to the socket 302 in such a way as to orient the foot 34 as hereinbefore described. However, the foot can be articulated in any appropriate direction to accommodate the foot to the surface of the tissue being sutured. The articulation permits the foot to rest flat on the tissue for proper support for the needle as it exits the tissue in line with the aperture or eye 42. Upon lifting the instrument, the spring 305 will return the foot to the proper orientation relative to the blade.

Figure 13:
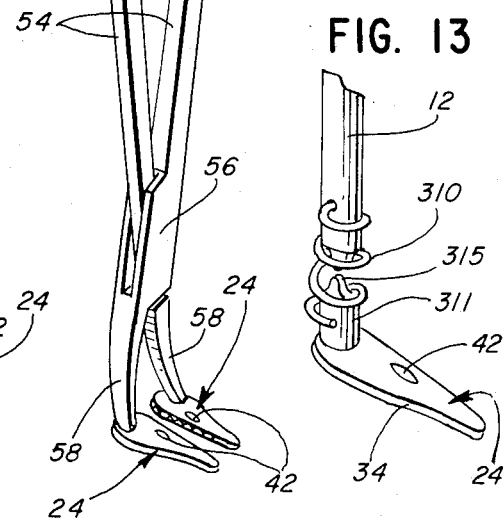
FIG. 13 is a perspective view illustrating the foot at the distal end of one of the forceps blades being resiliently connected.

FIG. 13 has a coil spring 310 anchored at one end to the blade 12, bridges the gap 315 between the foot and blade, and is fastened at the other end to the foot 34 or stub 311 on the foot. The spring orients the foot to rest in the normal position heretofore described. Placing the foot against a tissue will orient the foot to the slope of the tissue to provide a planar surface between the foot and the tissue for suturing.

Different types of joints and resilient connections are contemplated within the scope of the invention.

FIGS. 8-12 illustrate various configurations of feet 24, various locations of apertures or eyes 42 and various mounting positions of the feet onto the distal ends of the forceps blades.

More particularly, FIG. 8 shows feet 24A to be substantially narrow through the entire length thereof, with the feet mounted centrally to the forceps blades 12 near the posterior ends of the feet. Apertures 42 are located substantially in line with the forceps blades, forwardly of the blades and generally intermediate the ends of the feet.

FIG. 9 illustrates feet 24B to be substantially wider, with the left-hand foot including a series of apertures 42 extending across the foot, and the right-hand foot having a single, continuous aperture 42' extending substantially across the width of the foot. Continuous aperture 42' is serrated along the front and rear edges thereof to provide V-shaped constraining means similar to the V-shaped front and rear ends of apertures 42. With either the array of apertures in the left-hand foot in FIG. 9, or the continuous aperture 42' in the right-hand foot, multiple locations are provided in a transverse direction for receiving and constraining a needle during a suturing operation.

FIG. 10 illustrates feet 24C of a generally rectangular shape. The forceps blades 12 are mounted to the feet in a generally central location. The left-hand foot has an aperture or eye 42 located generally at each corner of the rectangular shape of the foot, two apertures being in front of the forceps blade and two being behind the blade. The right-hand foot shows a singular aperture 42 both in front of and behind the forceps blade. Again, these alternatives provide different locations for receiving and capturing a needle during a suturing operation.

FIG. 11 shows another rectangular configuration of feet 24D, but both feet are identical with a single aperture located to the right of the point of mounting the forceps blade to the respective foot. Again, this affords the surgeon another array of apertures for accommodating a particular operation.

Lastly, FIG. 12 shows feet 24E which are generally disc-shaped with no apertures in the feet. The medial edges 32' between the feet are generally straight and parallel. Such rounded feet may be used in a given application to apply counter-pressure to a specific localized area to stabilize the tissue in that area.

In all of the embodiments shown in FIGS. 8-12, the feet include generally parallel medial edges, and the feet are generally flat and extend generally transverse to the respective forceps blades.

It will be understood that the invention may be embodied in other specific forms without departing from the spirit or central characteristics thereof. The present examples and embodiments, therefore, are to be considered in all respects as illustrative and not restrictive, and the invention is not to be limited to the details given herein.

I claim:

1. A forceps-type surgical instrument, comprising:
   a pair of forceps blades, each forcep blade having a proximal end and a distal end, said forceps blades being coupled together at their proximal ends and being spreadable and closable at their distal ends; and
   a foot member operatively connected on the distal end of each forcep blade, each foot member extending transversely outwardly of the forep blade, said respective foot members having enlarged working surfaces lying in a common plane for facilitating the application of counter-pressures during surgical procedures.

2. The instrument of claim 1 wherein said working surfaces of the foot members are generally flat and wherein the common plane is generally transverse to the forceps blades.

3. The instrument of claim 1 wherein each foot member has an inwardly facing, medial edge, and wherein said medial edges are generally parallel to each other.

4. The instrument of claim 3 wherein at least a portion of the inwardly facing, medial edge of each foot member is serrated.

5. The instrument of claim 4 wherein the outwardly facing, lateral edge of each foot mmember is smooth.

6. The instrument of claim 3 wherein the outwardly facing, lateral edge of each foot member tapers forwardly toward a frontal tip of each foot member.

7. The instrument of claim 1 wherein each foot member is generally flat and extends generally perpendicular to the attached forcep blade.

8. The instrument of claim 1, wherein at least one foot member has at least one aperture for receiving and guiding a needle, suture and the like therethrough.

9. The instrument of claim 8 wherein each foot member is elongated and has a forward, anterior end and a rearward, posterior end, one foot member is mounted to each blade nearer the posterior end thereof, and said aperture is located forwardly of the point of mounting of said one foot member to the respective forcep blade.

10. The instrument of claim 9 wherein said aperture is located near the inner, medial edge of said one foot member.

11. The instrument of claim 9, wherein each foot member has at least one aperture therein, and wherein at least one of said apertures is located fowardly toward the anterior end of one foot member, and at least one of said apertures is located rearwardly toward the posterior end of one foot member.

12. The instrument of claim 8 wherein each said foot member has an outer, lateral edge and an inner, medial edge, and said aperture is located between the lateral edge of said one foot member and the point of mounting the respective blade thereto.

13. The instrument of claim 8 wherein each said foot member has an outer, lateral edge and an inner, medial edge, and said aperture is located between the medial edge of said one foot member and the point of mounting the respective blade thereto.

14. The instrument of claim 8 wherein each said foot member has forward, anterior ends and said aperture is located between the anterior end of said at least one foot member and the point of mounting the respective blade thereto.

15. The instrument of claim 8 wherein each said foot member has rearward, posterior ends, and said aperture is located between the posterior end and the point of mounting the respective blade thereto.

16. The instrument of claim 8 wherein each said foot member is generally rectangular and includes one of said apertures near each corner of said one foot member.

17. The instrument of claim 8 wherein each said foot member has an outer, lateral edge and an inner, medial edge, and one of said aperture is located near each said edge.

18. The instrument of claim 1 wherein each said foot member is generally disc shaped and the blades are respectively mounted thereto generally concentric thereof.

19. The instrument of claim 1 wherein each said foot member is resiliently mounted on said blade and are oriented with respect to eah other such that the medial edges of said foot members are generally parallel, and wherein said foot members can be moved relative to said blades upon contact with tissue or the like.

20. The instrument of claim 1 wherein said foot members are articulated relative to said blades.

21. The isntrument of claim 20 wherein resilient means are provided to return the foot members to an initial orientation.

22. The instrument of claim 20 wherein the articulation is provided by a ball and socket connection between the foot members and the blades.

23. A forceps-type surgical instrument, comprising:
a pair of forceps blades coupled together at their proximal ends and spreadable and closable at their distal ends;
a generally flat foot member mounted on the distal end of each blade and extending in a common plane generally transversely outwardly of the blades to enlarge the working area thereof and to facilitate the application of counter-pressures during surgical operations, each foot member including a forward, anterior end, a rearward, posterior end, an inwardly facing medial edge and an outwardly facing lateral edge, the medial edge of one foot member being generally parallel with the medial edge of the other foot member; and
at least one aperture in at least one of said foot members for receiving and guiding a needle, suture and the like during surgical operations therewith.

24. The instrument of claim 23 wherein at least a portion of the inwardly facing medial edge of each of said foot members are serrated.

25. The instrument of claim 24 wherein the outwardly facing lateral edge of each of said foot members are smooth.

26. The instument of claim 23 wherein the outwardly facing lateral edge of each of said foot members taper forwardly toward a frontal tip of the foot member.

27. The instrument of claim 23 wherein said aperture is located forwardly of the point of mounting said one foot member to the respective blade 28. The instrument of claim 27 wherein said aperture is located near the inner, medial edge of said one foot member.

29. The instrument of claim 23, including at least one of said apertures located forwardly and rearwardly of the point of mounting the respective blade to the foot member.

30. The instrument of claim 23 wherein said aperture is located between the lateral edge of said one foot member and the point of mounting the respective blade thereto.

31. The instrument of claim 23 wherein said aperture is located between the medial edge of said one foot member and the point of mounting the respective blade thereto.

32. The instrument of claim 23, including a plurality of said apertures arranged in an array transversely across said one foot member.

33. The instrument of claim 19 wherein each said foot member is articulated relative to said blades.

34. The instrument of claim 19 wherein each said foot member is resiliently mounted on said blades.

35. The instrument of claim 19 wherein each said foot member is mounted on said blades by a ball and socket connection.

36. A forceps-surgical instrument, comprising:
a pair of forceps blades coupled together at their proximal ends and separable and closable at their distal ends;
a foot member mounted on the distal end of at least one of said blades and extending transversely outwardly of the blade; and
at least one aperture in said one foot member for receiving and guiding a needle, suture and the like therethrough, said aperture including a narrow portion for frictionally capturing and holding the needle.

37. The instrument of claim 36 wherein said narrow portion of the aperture is generally V-shaped for capturing various sizes of needles.

* * * * *